(12) United States Patent
Nakashima et al.

(10) Patent No.: US 8,753,855 B2
(45) Date of Patent: Jun. 17, 2014

(54) METHOD FOR DETACHING CULTURED CELLS, CELL DETACHMENT DEVICE USED IN SAID METHOD FOR DETACHING CULTURED CELLS, AND INCUBATOR

(75) Inventors: Naotoshi Nakashima, Fukuoka (JP); Tsuyohiko Fujigaya, Fukuoka (JP); Kouji Nakazawa, Kitakyushu (JP); Yasuro Niidome, Fukuoka (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 13/582,337

(22) PCT Filed: Feb. 28, 2011

(86) PCT No.: PCT/JP2011/054550
§ 371 (c)(1),
(2), (4) Date: Aug. 31, 2012

(87) PCT Pub. No.: WO2011/108503
PCT Pub. Date: Sep. 9, 2011

(65) Prior Publication Data
US 2012/0329123 A1    Dec. 27, 2012

(30) Foreign Application Priority Data
Mar. 1, 2010    (JP) ................. 2010-044046

(51) Int. Cl.
C12N 13/00    (2006.01)
C12M 1/00    (2006.01)
C12M 1/42    (2006.01)
C12M 3/00    (2006.01)

(52) U.S. Cl.
USPC .................. 435/173.9; 435/303.1

(58) Field of Classification Search
None
See application file for complete search history.

(56) References Cited

FOREIGN PATENT DOCUMENTS

| | | |
|---|---|---|
| JP | 5-244938 A | 9/1993 |
| JP | 2006-314204 A | 11/2006 |
| JP | 2008-237209 A | 10/2008 |
| WO | WO 2009/081592 A1 | 7/2009 |

OTHER PUBLICATIONS

Fujigaya et al. WO 2009/081592, JPO machine translation.*
Hosokawa et al. "Nondestructive isolation of single cultured animal cells by femtosecond laser-induced shockwave", Applied Physics A 79: 795-98, 2004.*
Hu et al. "Chemically functionalized carbon nanotubes as substrates for neuronal growth", Nano Letters 4(3): 507-11, 2004.*
Kam et al. "Carbon nanotubes as multifunctional biological transporters and near-infrared agents for selective cancer cell destruction", PNAS 102(33): 11600-5, 2005.*
Hopp et al. "Survival and proliferative ability of various living cell types after laser-induced forward transfer", Tissue Engineering 11(11/12): 1817-1823, 2005.*
Zhang et al. "Theory of shock wave propagation during laser ablation", Physical Review B 69: 235403-1-235403-9, 2004.*
International Search Report issued in PCT/JP2011/054550 dated May 17, 2011.
Terada et al., "Multiwalled carbon nanotube coating on titanium", Bio-Medical Materials and Engineering, 2009, vol. 19, No. 1, pp. 45-52.

* cited by examiner

Primary Examiner — Ruth Davis
Assistant Examiner — Emily Cordas
(74) Attorney, Agent, or Firm — Birch, Stewart, Kolasch & Birch, LLP

(57) ABSTRACT

Disclosed is a method for detaching cultured cells that can selectively detach cultured adhered cells. The scaffold to which the cells adhere is configured from at least a cell adhesion factor containing carbon nanotubes, and by means of radiating laser light in a spot shape on the scaffold in a region where cells are adhered, a shock wave is generated by the heat arising by means of the photothermal conversion of the carbon nanotubes, and by means of this shock wave, the cells are caused to be in a non-adhered state.

10 Claims, 10 Drawing Sheets

Fig.6
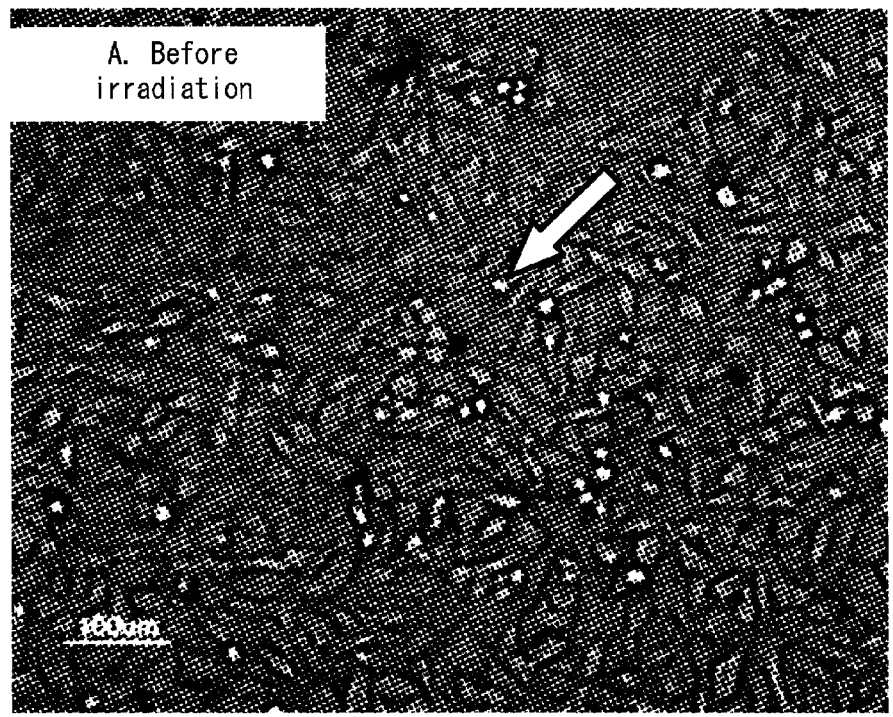
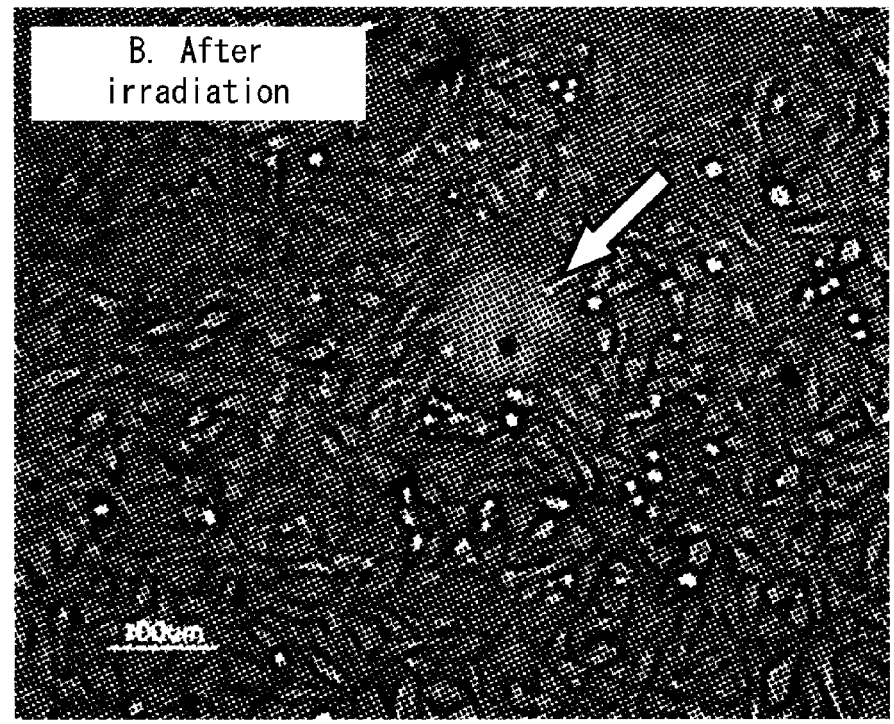

Fig.7
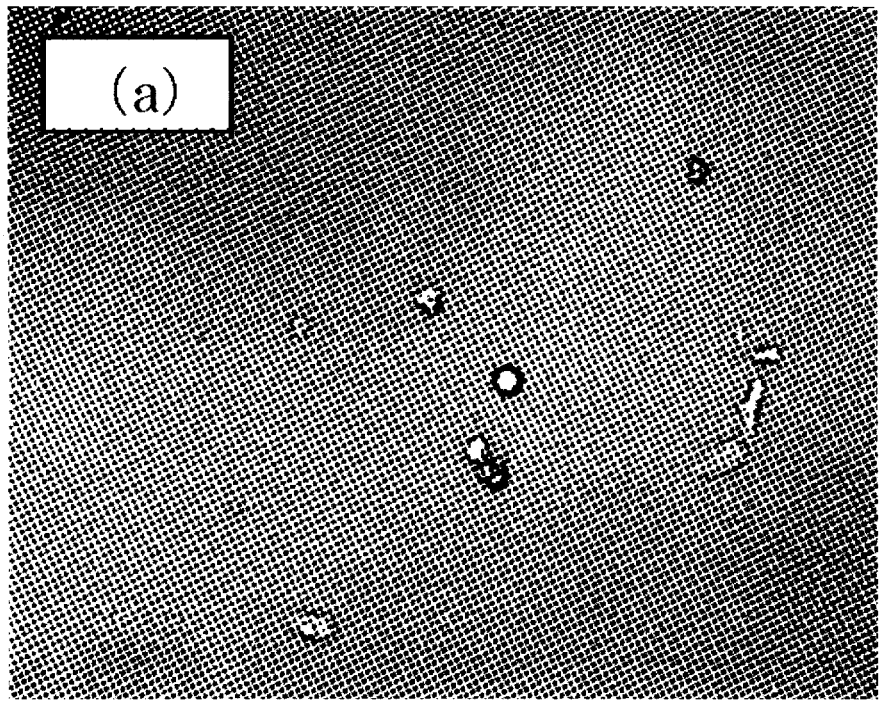
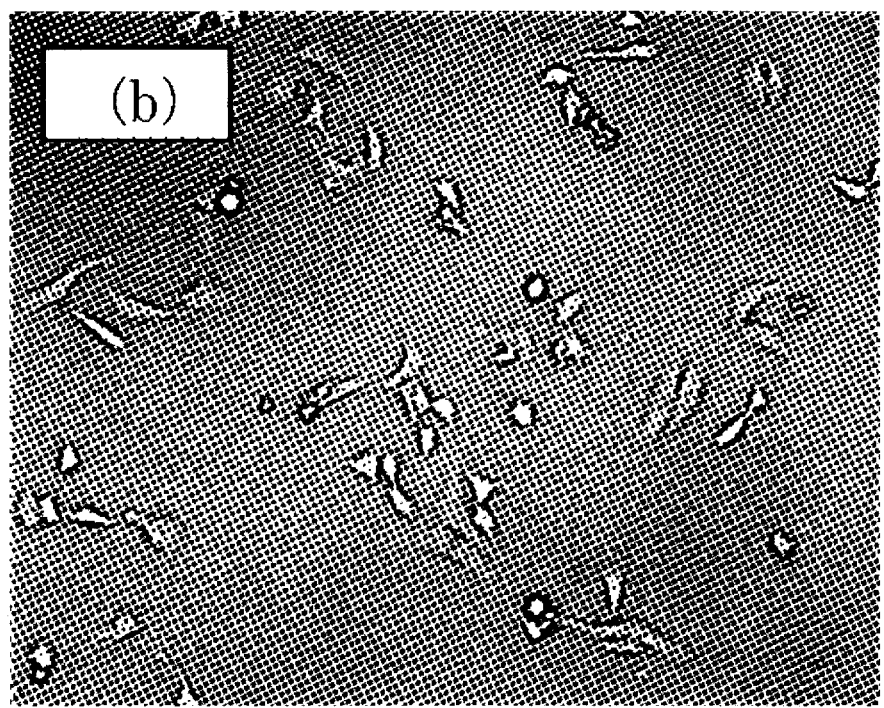

Fig.9
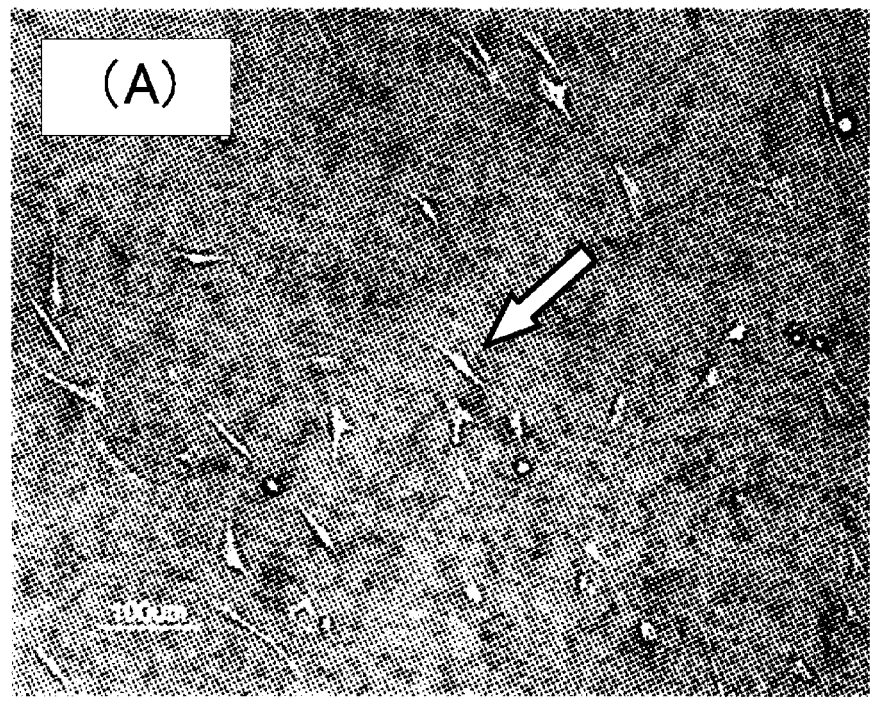
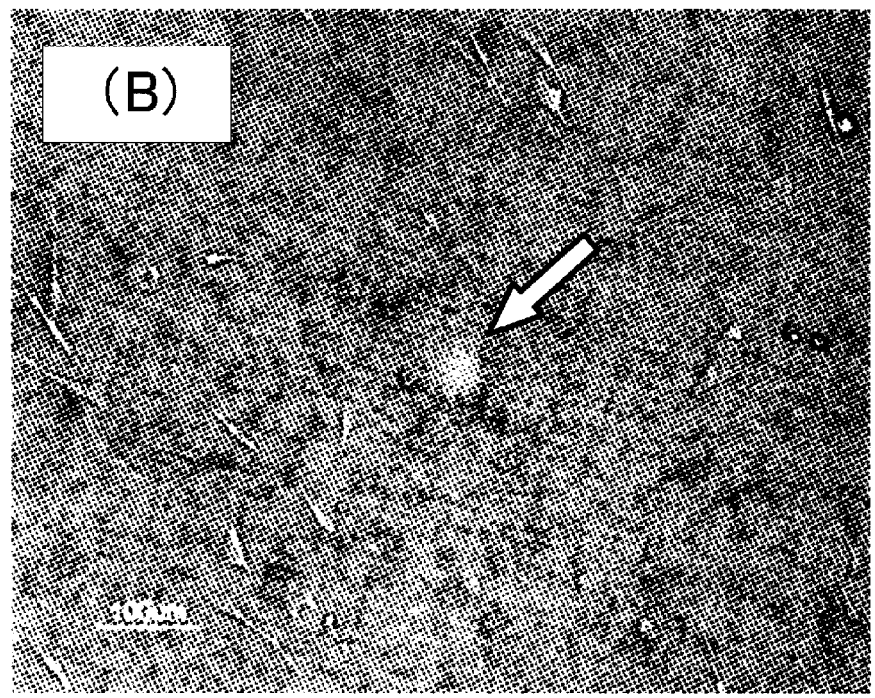

|  | Cell Detachment | Adehesion To Lid | Cells Dead or Alive? | Multiplication of Target Gene by PCR |
|---|---|---|---|---|
| 30mw | Not Detached | Not Adhered | Multiplied Thereafter | Done |
| 35mw | Detached | Not Adhered | Alive | Done |
| 39mw | Detached | Adhered | Alive | Done |
| 40mw | Detached | Adhered | Dead | Done |
| 500mw | Detached | Adhered | Dead | Done |
| 510mw | Detached | Adhered | Dead | Not Done |

Fig.12

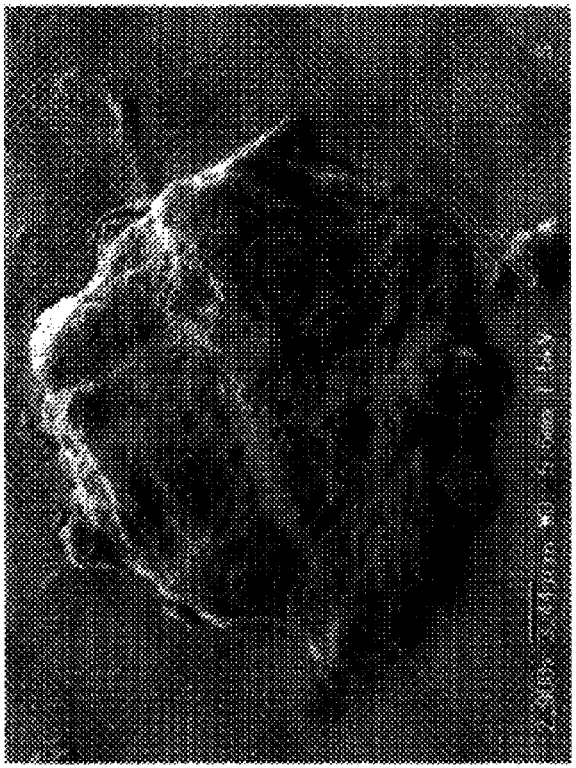

Electroscopic Picture of HeLa Cell Collected from Substrate After irradiation with laser light

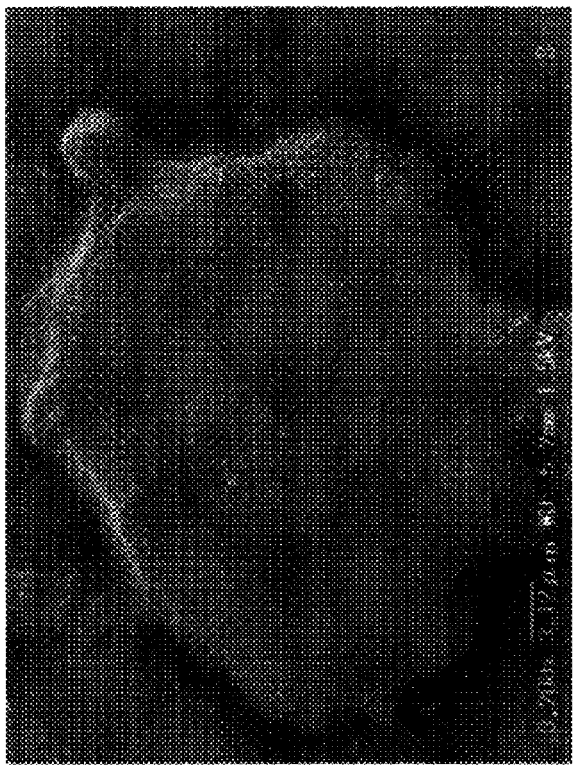

Electroscopic Picture of HeLa Cell Before irradiation with laser light

These pictures indicate that a nucleic acid needed for gene analysis, etc. can be collected because the shape of the cell collected from a substrate disposed at the upper portion of a culture medium.

METHOD FOR DETACHING CULTURED CELLS, CELL DETACHMENT DEVICE USED IN SAID METHOD FOR DETACHING CULTURED CELLS, AND INCUBATOR

TECHNICAL FIELD

The present invention relates to a detachment method for selectively detaching an adherent cell cultured in an incubator, a cell detachment device to be used for the detachment method, and an incubator to be used therefor.

BACKGROUND TECHNOLOGY

Heretofore, cell cultures have frequently been carried out in the field of medicine, pharmacology, biology, etc., in order to multiply or sustain cells separated from multicellular organisms in an in vitro environment.

As a typical example of cell cultures, there may be mentioned a cell culture, a so-called adhesion culture, which is involved in placing a liquid culture medium in an incubator with a thin film formed on its inner bottom with a biocompatible material or the like, and inoculating cells on the liquid culture medium, followed by incubating the cells on the thin film that is used as a scaffold.

The cells inoculated in the manner as described above may multiply by means of cell division and expand on the scaffold, resulting in the formation of a layer of the cells.

The cells multiplied as above in the film form are required to be detached from the scaffold in the incubator in order to allow a further use for experiments or another culture.

The cultured cells attached to the scaffold with a comparably weak adhesion force, on the one hand, may be detached from the scaffold by physically scratching an cultured cells off the scaffold with a tool called a scraper. The cultured cells attached thereto with a comparably strong adhesion force, on the other hand, have conventionally been detached from the scaffold by decomposing an adhesion factor between adhered cells and the scaffold with a protease including, for example, collagenase or trypsin.

The detachment method using the protease, however, may encounter difficulties in decomposing the adhesion factor upon detachment of the adhered cells from the scaffold because the protease may involve the risk of decomposing and destructing proteins other than the adhesion factor, such as membrane proteins, which are present on the cell surfaces.

Therefore, a method that does not require the use of the protease has been proposed, which is involved in the detachment of cells attached to a scaffold by delivering an ultrasonic vibration to an incubator from upwards (for example, see Patent Document No. 1).

The method using the ultrasonic vibration is reported as capable of detaching the adhered cells from the scaffold without destroying proteins such as membrane proteins on the surfaces of the cells.

PRIOR ART REFERENCES

Patent Document No. 1: JP 2006-314204 A1

SUMMARY OF INVENTION

The conventional detachment method using ultrasonic vibration, however, may encounter difficulties in selectively detaching cells multiplied on the scaffold.

The conventional detachment method using the ultrasonic vibration as described above, however, may involve a risk of contamination of cells other than the cells desired to be detached from the scaffold because the ultrasonic vibration may propagate and spread over the whole area of the incubator, thereby detaching the desired cells and the non-desired cells as well.

Therefore, the present invention has the object to provide a detachment method for selectively detaching a cultured cell.

The present invention has other objects to provide a device and an incubator for selectively detaching the cultured cell.

In order to achieve the objects as described above, the present invention provides a detachment method of cultured cells, which is involved in a method for the detachment of a cultured cell for selectively detaching an adherent cell cultured in a liquid culture medium in an incubator, comprising: forming a scaffold for attaching the adherent cell with a cell adhesion factor containing at least a nanocarbon, and irradiating a region of the scaffold to which an adherent cell adheres with a laser beam in a spot shape to bring the adherent cell into a detached state by shock waves generated by heat produced by means of a photothermal conversion of the nanocarbon caused to occur by irradiation with the laser beam; wherein the laser beam is irradiated at an intensity that allows the detached cell to catapult off from a liquid surface of the liquid culture medium by an action of the shock waves.

The present invention is involved in a method for the detachment of a cultured cell for selectively detaching an adherent cell cultured in a liquid culture medium in an incubator, comprising: forming a scaffold a scaffold for attaching the adherent cell with a cell adhesion factor containing at least a nanocarbon; and irradiating a site of the scaffold to which the adherent cell adheres with a laser beam in a spot shape, thereby causing the site of the scaffold to disappear by heat produced by a photothermal conversion of the nanocarbon caused to occur by irradiation with the laser beam and causing the site of the scaffold irradiated with the laser beam to work as an ablator to bring the adherent cell located in the site of the scaffold into a detached state while protecting the cell from the heat; wherein the laser beam is irradiated at an intensity that allows the detached cell to catapult off from the liquid surface of the liquid culture medium by an action of the shock waves.

The present invention is involved in a method for the detachment of a cultured cell for selectively detaching an adherent cell cultured in a liquid culture medium in an incubator, comprising: forming a scaffold for attaching the adherent cell with a cell adhesion factor containing at least a nanocarbon; and irradiating a region of the scaffold to which the adherent cell adheres with a laser beam in a spot shape to bring the adherent cell into a detached state by shock waves generated by heat produced by a photothermal conversion of the nanocarbon caused to occur by irradiation with the laser beam; wherein an amount of the liquid culture medium is adjusted to a depth that allows the adherent cell attached to the site of the scaffold to catapult off from the liquid surface of the liquid culture medium by means of shock waves generated by irradiation with the laser beam.

The present invention relates to a method for the detachment of a cultured cell for selectively detaching an adherent cell cultured in a liquid culture medium in an incubator, comprising: forming a scaffold for attaching the adherent cell with a cell adhesion factor containing at least a nanocarbon; and irradiating a site of the scaffold to which the adherent cell adheres with a laser beam in a spot shape, thereby causing the site of the scaffold to disappear by heat produced by a photothermal conversion of the nanocarbon caused to occur by irradiation with the laser beam and causing the site of the scaffold irradiated with the laser beam to work as an ablator to bring the adherent cell located in the site of the scaffold into a detached state while protecting the cell from the heat; wherein an amount of said liquid culture medium is adjusted to a depth that allows the adherent cell attached to the site of the scaffold to catapult off from the liquid surface of the liquid culture medium by means of shock waves delivered by irradiation with the laser beam.

The present invention is involved in the method for the detachment of the cultured cell, wherein plural cells adhere to the scaffold; and an region of the scaffold to which a single cell adheres is irradiated with the laser beam, isolating the single cell from the other plural cells.

The present invention is involved in the method for the detachment of the cultured cell, wherein the incubator is provided with an opposite surface facing and opposite to the liquid surface of the liquid culture medium; and the cell catapulted off from the liquid surface of the liquid culture medium by means of the shock waves generated by irradiation with the laser beam is caused to adhere to the opposite surface.

The present invention is the detachment method of the cultured cells, wherein the laser beams possess a wavelength of near infrared.

The cell detachment device according to the present invention comprises: an incubation section composed of an incubator whose inside is coated with a cell adhesion factor containing at least a nanocarbon, which is provided with a scaffold to which a cell adheres, and which has an opposite surface facing and opposite to the liquid surface of the liquid culture medium for incubating cells adhering to the scaffold; a microscope section for observing cells in the incubator; a waveform signal output section for sending a predetermined waveform signal; and a laser beam source section for generating a laser beam whose intensity is modulated in accordance with a waveform signal outgoing from the waveform signal output section; wherein: the scaffold of the incubator is irradiated with the laser beam generated from the laser beam source section; the cultured cell is detached from the scaffold by means of shock waves generated by heat produced by a photothermal conversion of the nanocarbon caused to occur by irradiation with the laser beam at an intensity at which the adherent cell catapults off from the liquid surface of the liquid culture medium; and the adherent cell catapulted off therefrom is caused to adhere to the opposite surface.

The present invention presents the merits that it provides the detachment method of the cultured cells capable of selectively detaching the adherent cell cultured, the cell detachment device, and the incubator.

BRIEF DESCRIPTION OF THE ACCOMPANYING DRAWINGS

FIG. 6 is an explanatory drawing showing the cell before and after the detachment of the cultured cell from the scaffold.

FIG. 7 is an explanatory drawing showing the cell obtained by re-incubation of the detached cell.

FIG. 9 is an explanatory drawing showing the cell before and after the detachment of the cultured cell.

FIG. 12 shows electron micrographic pictures of outer outlooks of a cell recovered before and after irradiation with laser beams.

MODES FOR CARRYING OUT THE INVENTION

The present invention has an object to provide a detachment method for selectively detaching an adherent cell cultured in an incubator.

As described above, the cells incubated under adhesion culture are formed and aggregated in the form of a group of innumerable cells in a layer by repeated events of cell division and multiplication on a scaffold.

Among the innumerable cells multiplied, some cells may be subject to mutation or an error in a reproduction of a gene. Almost all of those cells cause apoptosis, but a small number of cells may acquire a very interesting character or phenotype.

In the event where a target gene is introduced into a cell in a shotgun-like manner, particular cells have to be collected from an innumerable number of cultured cells.

Under such circumstances, the detachment method of the cultured cells according to a working embodiment of the present invention may selectively detach the adherent cells of interest and bring them into a non-attached state, thereby readily collecting the adherent cells of interest.

Figure 1:
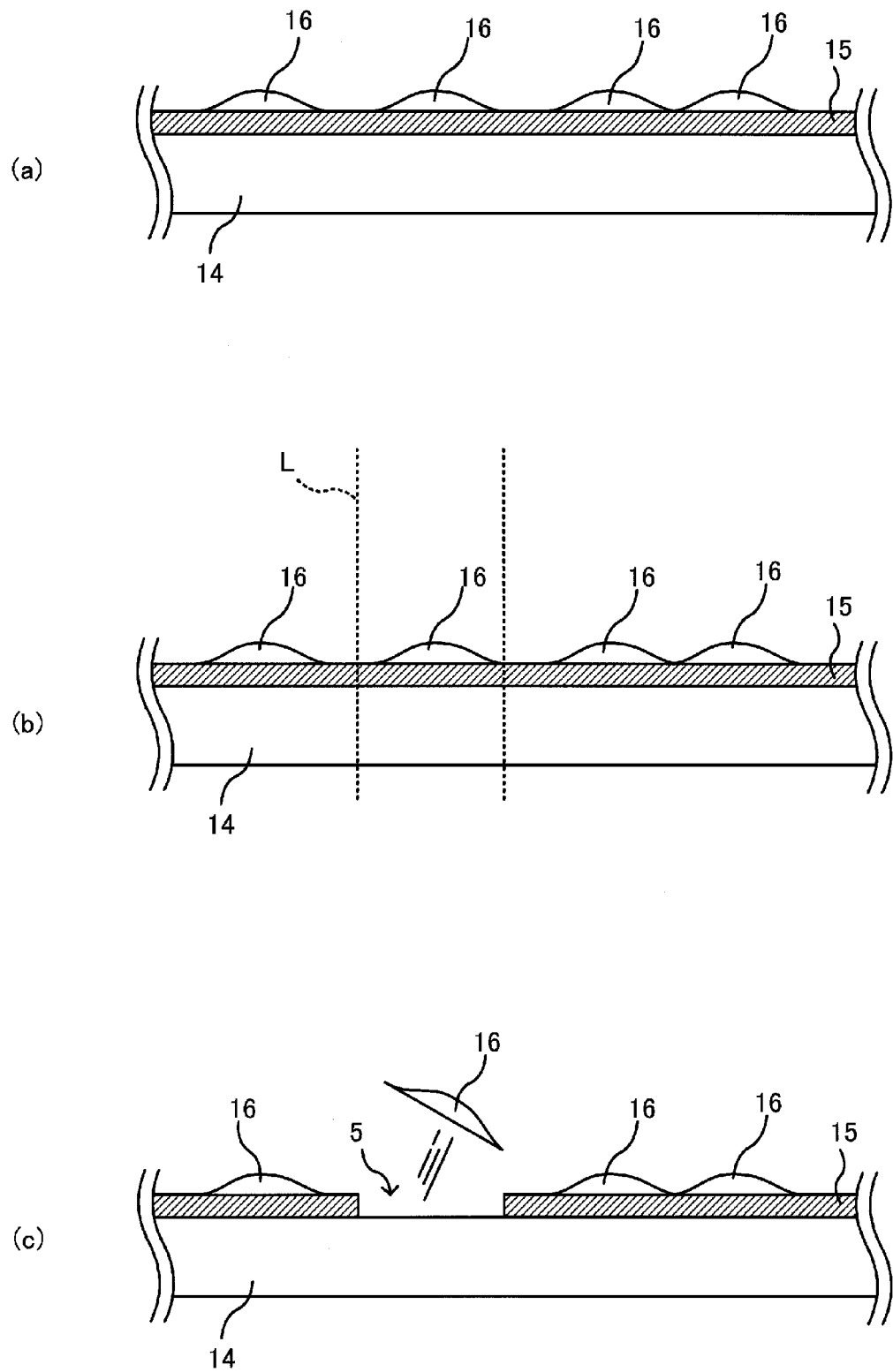
FIG. 1 is a schematic illustration showing the concept of detachment by the detachment method of the cultured cell according to the present invention.

More specifically, the detachment method of the cultured cells according to the working embodiment of the present invention is characterized by carrying out an adhesion culture in a manner as shown in FIG. 1(a) on a scaffold formed with a cell adhesion factor containing at least a nanocarbon, to which the cultured cells are to adhere. In FIG. 1, numeral 16 indicates cultured cells, numeral 15 indicates a scaffold, and numeral 14 indicates an incubator. Then, as shown in FIG. 1(b), the scaffold 15 is irradiated with laser beams in a spot shape at a site to which the cultured cell of interest to be detached is attached.

Upon irradiation of the site of the scaffold with the laser beams, the heat is produced by the photothermal conversion effect of the nanocarbon contained in the scaffold, generating shock waves by a photo-acoustic effect.

As shown in FIG. 1(c), the cell 16 of interest sought to be detached is separated from the scaffold 15 and the incubator 14 by the shock waves delivered to the site of the scaffold, and the cell 16 of interest is brought into a non-attached state.

More specifically, upon the irradiation of the nanocarbon contained in the scaffold with the laser beams, the scaffold is destructed by itself by the heat produced by way of the photothermal conversion of the nanocarbon contained therein, and the cultured cell adhered to that scaffold is caused to be detached from the scaffold by the delivery of the shock waves generated by its photo-acoustic effect. In particular, the nanocarbon is so superior in an efficiency of photothermal conversion that the effect of the laser beams on the photothermal conversion can be induced by the laser beams of a relatively low energy. Therefore, the cultured cell can be detached by the shock waves while protecting the cells from damages caused by the laser beams during incubation.

The present invention has the merits that the adherent cell can be detached and collected while preventing the adherent cell from contamination or other adverse influences without causing damages by using the nanocarbon and irradiating the adherent cell at a pin point with laser beams.

In particular, the present invention provides a minimally invasive and efficient cell manipulation technique and can be applied to a wide range of cell engineering including regenerative medicine, disease analysis, drug developments, and so on.

The terms "cell adhesion factor" as used herein are intended to mean in general terms a biocompatible material that can be used as a scaffold for cells during incubation, but they are herein intended in particular to mean a biocompatible material containing at least a nanocarbon. More specifically, the cell adhesion factor may include, but not be limited to, a mixture of a biocompatible material as generally used for the formation of a scaffold with a nanocarbon or a nanocarbon alone. The biocompatible material to be used therefor may include, but not be limited to, a collagen or agar. The scaffold may be formed by fixing or disposing the cell adhesion factor on an inner surface of the incubator (hereinafter referred to as "cell adhesion surface", too), including, but not be limited to, an inner bottom surface thereof, to which a cell adheres.

The scaffold may be formed by coating the inner surface of the incubator with the cell adhesion factor. A coating technique to be used for the present invention may not be limited to a particular one, and any coating technique may be used as long as it can form a thin film of the cell adhesion factor on the inner surface of the incubator. The scaffold may also be formed by pre-forming a thin film of the cell adhesion factor and arranging the pre-formed thin film at a desired location inside the incubator.

The nanocarbon structuring the cell adhesion factor may include, but not be limited to, a carbon nanotube, graphene, carbon black, and the like. In particular, the carbon nanotube is preferred because it is highly efficient in a photothermal conversion due to its tubular structure, thereby enabling an efficient generation of shock waves.

The carbon nanotube is a substance having a structure in which a graphene sheet is rounded in a tubular shape. The carbon nanotube may be classified by its structure into a single-walled carbon nanotube (SWNT) or a multi-wall carbon nanotube (MWNT) having a multiple layer of the graphene sheets rounded in a coaxially tubular shape. For a working embodiment of the present invention, each of the single-walled carbon nanotube and the multi-wall carbon nanotube may be used without limitation to a particular one. It is to be noted herein that, as the carbon nanotube has the tendency that the larger the number of the layers structuring the multi-wall carbon nanotube the longer it will take a time to destruct the carbon nanotube due to an increase in the energy required for destruction, the single-walled carbon nanotube may be used preferably in the event that the cultured cells are intended to be detached by laser beams having the possible lowest energy.

The incubator to be used for the adhesion culture of cells according to the present invention may be designed in such a way that a scaffold formed with the cell adhesion factor containing at least the nanocarbon is formed on the cell adhesion surface to which cells are caused to adhere. As the incubator, there may be used any container that has been conventionally used for cell cultures, and they may include, for example, an incubation bottle, a glass dish, a glass bottom dish, and so on. The material of the incubator may not be limited to a particular one as long as the scaffold can be formed on its inner surface, but it has to be at least a transmittable material through which laser beams can pass toward the scaffold.

The detachment method of the cultured cells according to a working embodiment of the present invention may destruct the scaffold formed with the nanocarbon by way of the photothermal conversion caused to occur in the nanocarbon of the scaffold by the irradiation of the scaffold for cells with laser beams during incubation of the cells. The photothermal conversion of the nanocarbon may generate shock waves, leading to the detachment of the cultured cells from the scaffold. It may be considered that the cell is detached from the scaffold by the event that it is detached from the scaffold due to the reaction of the shock waves delivered, although it may depend upon the intensity of the laser beam to be irradiated thereto, or it is detached therefrom by the formation of a gap due to the destruction of the scaffold itself as shown in FIG. 1(c).

From a different point of view, the present invention can be said to relate to a detachment method for detaching the cultured cells from the scaffold by inducing an ablation in the nanocarbon causing an occurrence of the photothermal conversion by the irradiation with the laser beams.

More particularly, the present invention is involved in the detachment method of the cultured cell for selectively detaching the adherent cell incubated in the incubator, wherein the incubator is provided with the scaffold formed with the cell adhesion factor containing at least the nanocarbon, to which the cells are caused to adhere, and a site of the scaffold to which the adherent cell adheres is irradiated with the laser beams in a spot-like shape, thereby causing the scaffold locating at the site thereof to disappear due to the heat generated by the photothermal conversion of the nanocarbon and bringing the cultured cell adhering to the site thereof into a detached state while protecting the cultured cell from the produced heat by allowing the scaffold at the irradiated site to function as an ablator.

In other words, the present invention is involved in the technique that detaches the cells by allowing the nanocarbon to function as an ablator and causing the scaffold to disappear while protecting the cultured cells from the heat.

The detachment method according to the present invention enables the detachment of the cells present within a spot-shaped range of the scaffold by the irradiation of the range with the laser beams by adjusting a beam size of the laser beam and changing a size of the spot-shaped range. For instance, it is made feasible to acquire a single cell from plural cells by adjusting the size of the spot-shaped range to a size encompassing the single cell and irradiating the spot-shaped range with the laser beams.

Although a wavelength of the laser beam irradiating the scaffold is not limited to a particular one, the laser beam of a near infrared wavelength is preferred. The near infrared light is so high in permeability through the living body that an adverse influence on cells can be reduced to the greatest possible extent.

The laser beam may be a continuous light or a pulsed light. In the case where the laser beam is a pulsed light, a high magnitude of energy may be delivered in a moment to the nanocarbon of the scaffold, enabling an efficient detachment of the cells. A pulse pattern in this case may be decided appropriately in accordance with the energy of the laser beam to be irradiated.

In the manner as described above, the detachment method of the cultured cells according to a working embodiment of the present invention can selectively detach the cells growing at a particular site of the incubator by irradiating the cells adhering to the particular site of the scaffold with the laser beams.

The cells as the object for detachment may be those which are being incubated in the liquid culture medium or those which are present in a state in which the liquid culture medium has been removed.

In particular, in the case where the cell being in the process of incubation in the liquid culture medium is to be detached, the laser beams may be irradiated at an intensity that may cause the cell to catapult off from the liquid surface of the liquid culture medium by the shock waves delivered. In other words, the irradiation of the laser beams having a sufficiently high intensity enables the cell to catapult off from the liquid surface of the liquid culture medium.

This technique is very useful for selectively acquiring a certain single cell from plural cells. In accordance with the present invention, a single cell desired to be acquired selectively from plural cells can be obtained readily by causing the single cell to catapult over from the liquid surface of the liquid culture medium and adhere to the opposite surface of the incubator containing the liquid culture medium, the opposite surface of the incubator being disposed opposite to the liquid surface of the liquid culture medium. It is to be understood herein that the opposite surface may include, for example, an inner wall surface of a lid of a culture plate or an incubation bottle. The opposite surface, however, is not limited to a particular one and may be equipped separately upon collection of the cell. Although cases may occur when the cells adhered to the opposite site are dead upon an impact on the opposite site by the shock waves, even such dead cells may be usefully applied to a genetic analysis or the like.

As an alternative method for catapulting the cell upwards over the liquid surface of the liquid culture medium, there may be mentioned, for example, a method for adjusting an amount of the liquid culture medium so as to comply with the depth of the liquid culture medium contained in the incubator which allows the cell to catapult off from the liquid surface thereof due to the shock waves generated by the irradiation of the laser beams. In another words, this alternative method allows a ready adhesion of the cell to the opposite surface thereof by reducing an amount of the liquid culture medium in the incubator to shorten a distance between the liquid surface thereof and the cell adhering to the opposite surface thereof and irradiating the scaffold with the laser beams. More specifically, the distance between the scaffold surface from which the cell catapults off from the liquid surface of the liquid culture medium and the liquid surface of the liquid culture medium, that is, a depth of the liquid culture medium, may be at maximum 2 mm, preferably 1 mm or shorter. In the event where the depth of the liquid culture medium is over 2 mm, it is difficult to make the cell catapulting off from the liquid surface of the liquid culture medium. On the other hand, the cell can be catapulted off from the liquid surface thereof in an easier way as the depth of the liquid culture medium is made as short as possible. In this respect, the minimal depth of the liquid culture medium may not be limited to a particular one, however, it is desired to make the liquid culture medium to be wet to such an extent that the cell and/or the surface of the scaffold are/is made somewhat wet upon adhesion of the cell to the opposite surface disposed opposite to the liquid surface of the liquid culture medium by utilizing the viscosity of the liquid culture medium. The minimal depth may be set to 0.01 mm for example.

The present invention provides a cell detachment device comprising an incubation section having the incubator coated at its inside with the cell adehesion factor containing at least the nanocarbon and equipped with the scaffold to which cultured cells adhere; a microscope section disposed so as to observe the cells within the incubator; a waveform signal output section disposed so as to send a predetermined waveform signal; and a laser beam source section sending the laser beam with its intensity modulated in accordance with the waveform signal generated from the waveform signal output section; wherein the cultured cell is made detachable from the scaffold of the incubator due to the shock waves generated by the heat produced by the photothermal conversion of the nanocarbon caused to occur by the irradiation of the scaffold with the laser beams.

The cell detachment device having the above structure enables a readily selective detachment of a single cell or plural cells from cultured cells by arranging for a laser beam to irradiate a scope of the scaffold so as to contain the single cell or the plural cells.

The following is a description regarding the detachment method for detaching an adherent cell, the cell detachment device, and the incubator to be used therefor by way of specific examples.

Example 1

This example is to make an explanation of an example in which a cell adhesion factor for forming a scaffold is composed of a single wall nanotube.

1. Preparation of a Solution Containing a Cell Adhesion Factor:

A solution containing the cell adhesion factor was prepared by mixing carboxylmethyl cellulose sodium salt (CMC-Na) with a single-walled carbon nanotube (SWNT). In this example, CMC-Na was added as a dispersing agent for the single-walled carbon nanotube and it does not function as a cell adhesion factor. Therefore, in this example, the cell adhesion factor consisted solely of the single-walled carbon nanotube.

The solution containing the cell adhesion factor was prepared in the following specific way. To 10 ml of water was added 1 mg of SWNT (Meijo Nanocarbon K.K.), and 3 mg of CMC-Na (Kishida Chemical K.K.) was added. The resulting mixture was then subjected to ultrasonic treatment for 120 minutes using a bath-type sonicater (Branson 5510) for dispersing the mixture. Thereafter, the dispersed mixture was centrifuged at 10,000×g for 15 minutes with a table-top type high-speed refrigerated centrifuge (3K30c; Kubota Shoji K.K.), and approximately 70% of the supernatant was recovered as a CMC-Na/SWNT dispersing solution.

2. Preparation of the Incubator:

A dish (35 mm Glass Base Dish; IWAKI) to be used as an incubator was sprayed with the CMC-Na/SWNT dispersing solution prepared previously, thereby forming a scaffold on an inner bottom surface of the dish.

More specifically, the dish was then placed on a heating face in a heating device set at 100° C. and sprayed with the above-prepared CMC-Na/SWNT dispersing solution with a sprayer toward the inner bottom surface of the dish.

The dish was sprayed with the CMC-Na/SWNT solution in 10 cycles, one cycle being set to 10 seconds consisting of 2 seconds for spraying and 8 seconds for evaporation of water. Alternatively, another dish was sprayed with the CMC-Na/SWNT solution in 30 cycles in the same manner as above.

Figure 2:
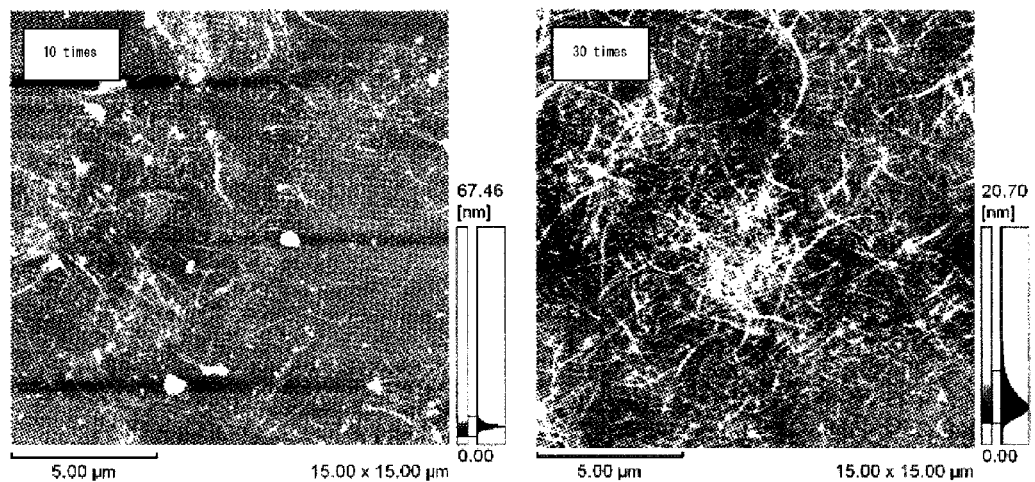
FIG. 2 is an explanatory drawing showing the cell adhesion factor attached to the inside of a culture vessel.

Each of the dishes treated as above was immersed in water for 2 days to remove excessive CMC-Na/SWNT and then dried in order to use for an incubator. A surface resistivity of the surface of each incubator for forming the scaffold was:

$10^5 \Omega/\square$ for the dish treated in 10 cycles and $5 \times 10^3 \Omega/\square$ for the dish treated in 30 cycles. By changing the cycle for treatment, an amount of immobilizing the SWNT was found to be controlled successfully. The result of AFM as shown in FIG. 2 also reveals that the amount of immobilizing the SWNT was controlled successfully.

Figure 3:
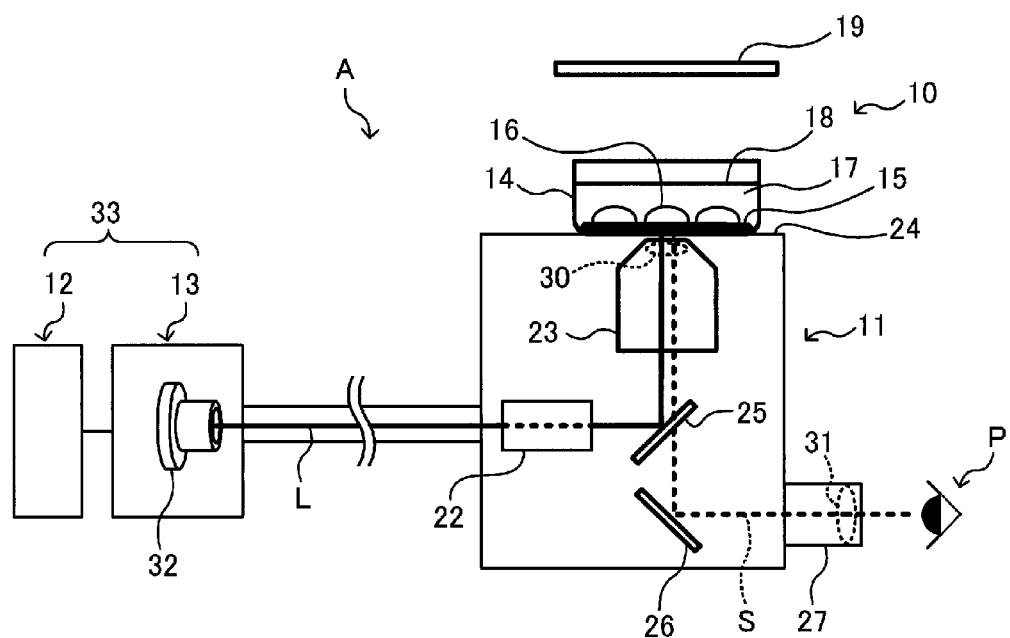
FIG. 3 is a schematic illustration showing the structure of a cell detachment device according to the present invention.

3. Cell Detachment Device:

The cell detachment device according to a working embodiment of the present invention will be described hereinafter by referring to the accompanying drawings. FIG. 3 is a schematic illustration showing the structure of the cell detachment device according to the present invention.

As shown in FIG. 3, the cell detachment device A is composed of the incubation section 10, the laser beam output section 33, and the microscope section 11.

The incubation section 10 is equipped with an incubator 14 of a dish shape, which is coated with the cell adhesion factor containing at least the nanocarbon on its inner surface and provided with a scaffold 15 to which cells adhere. FIG. 3 illustrates a state in which the cultured cells 16 adhere to the scaffold 15.

The incubator 14 is shown to be in such a state that a lid is removed and to contain a liquid culture medium for incubating the cells 16 inside the incubator 14.

Immediately above the incubator 14, a substrate 19 for cell collection is disposed so as to collect the cell 16 that was caused to catapult off from the liquid culture medium 17 by irradiation of the scaffold 15 with laser beams L and adhered to the scaffold 15. The cell collection substrate 19 is also disposed so as to function as the opposite surface facing and opposite to the liquid surface of the liquid culture medium.

In this working embodiment of the present invention, in particular, the cell collection substrate 19 may be used in the form of a sterilized flat plate. The flat plate was disposed and fixed with a support, although not shown, so as for its bottom surface to face the liquid surface 18 of the liquid culture medium 17. The distance between the liquid surface 18 and the cell collection substrate 19 may be adjusted appropriately so as to allow an adhesion of the cell 16 catapulted off from the liquid culture medium 17 in accordance with an intensity of irradiation with the laser beams L, an adhesion strength of the cells 16 to the scaffold, and the like.

Figure 4:
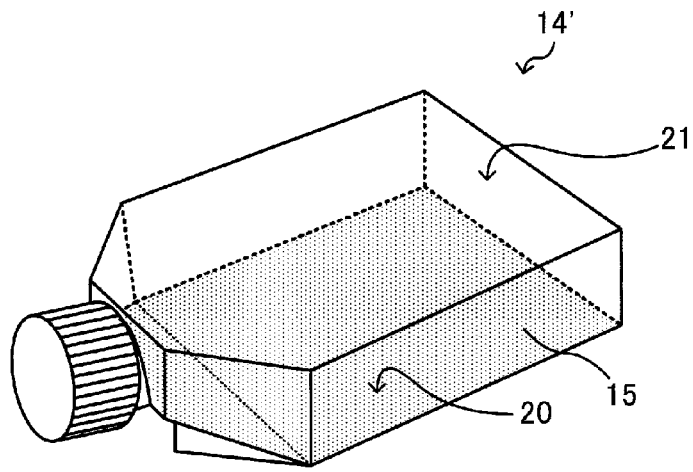
FIG. 4 is a schematic illustration showing an example of the culture vessel.

In this working embodiment of the present invention, the dish without a lid was used as the incubator 14, however, the incubator is not limited to such a lid-free dish as described above. For example, as shown in FIG. 4, there may also be used an incubator 14' of a tissue incubation flask type in which a scaffold 15 is disposed on a bottom surface portion 20. In this embodiment, an upper surface portion 21 of the incubator 14' works as an opposite surface facing and opposite to the liquid surface 18 of the liquid culture medium 17, in place of the cell collection substrate 19. Therefore, this embodiment is an example where no cell collection substrate 19 is needed to be formed separately. Alternatively, the incubator 14 of a dish type may be arranged so as for a dish lid to work as the opposite surface facing and opposite to the liquid surface 18 of the liquid culture medium 17. In summary, the cell collection substrate 19 may be disposed as needed.

The laser beam output section 33 is equipped with the laser beam source section 13 and the waveform signal output section 12.

The laser beam section 13 is arranged to send the laser beams L. Inside the laser beam source section 13, a laser beam output diode 32 is equipped to send the laser beams L of an intensity that corresponds to the waveform signal generated and sent by and from the waveform signal output section 12.

The waveform signal output section 12 is arranged to send a waveform signal to the laser beam source section 13 and connected to an input device, although not shown. An observer P can make access to the input device in order to adjust an output waveform and determine an output pattern of the laser beams L generated from the laser beam source section 13, an output intensity, an output duration, and so on.

The microscope section 11 is composed of a stage 24, an object optical system unit 23, a first mirror 25, a second mirror 26, an ocular optical system unit 27, and a beam diameter adjustment mechanism 22.

The beam diameter adjustment mechanism 22 is arranged so as to adjust a beam diameter of the laser beams L outgoing from the laser beam source section 13. The beam diameter of the laser beams L may be adjusted using a lens, an aperture, or the like in a conventional manner. The laser beams L with the beam diameter adjusted in the above manner was collimated and sent to the first mirror.

The first mirror 25 is disposed so as to reflect the laser beams L sent from the laser diameter adjustment mechanism 22 and lead the reflected laser beams L to the object optic system unit 23. The first mirror 25 may be provided with a wavelength-selective reflection film formed by vacuum deposition of a predetermined metal compound on a surface of a transparent substrate of a plate form made of glass, a plastic or the like. The wavelength-selective reflection film may possess properties of reflecting a light of a particular wavelength range and penetrating lights of other wavelength ranges.

Particularly, in this working embodiment of the present invention, the first mirror 25 with the wavelength-selective reflection film disposed thereon may be composed of a dichroic mirror reflecting the laser beams L, leading the reflected laser beams L to the object optic system unit 23.

The object optic system unit 23 is provided with an optic system that converges the incoming laser beams L reflected by the first mirror 25 into a range which the observer P is in the position to observe. The laser beams L are then sent to the stage 24.

The stage 24 may be composed of a table on which to put the incubator 14 in position. The stage 24 is provided with a hole through which a top portion of the object optic system unit 23 disposed below the stage 24 is allowed to expose to the incubator 14.

The laser beams L sent from the object optic system unit 23 are arranged to irradiate the scaffold 15 to which the cells 16 adhere in the incubator 14 disposed on the stage 24 through the hole of the stage 24, thereby detaching the cell 16 from the scaffold 15.

The stage 24 is disposed in such a manner that it is irradiated with illumination lights from an illumination apparatus (not shown). A portion of the illumination lights (hereinafter referred to as "observation light S") reflected by an object (such as the cell 16) within the observation field comes into the object optic system unit 23 through the hole formed in the stage 24.

The object optic system unit 23 is disposed so as to provide a surface for an intermediate image formed by the concentration of a luminous flux of the observation light S incoming through an object lens 30. The observation light S outgoing from the object optic system unit 23 is led to the first mirror 25.

The first mirror 25 is disposed so as to reflect a light having a predetermined wavelength (a light having a wavelength corresponding to that of the laser beam L) in the manner as described above. As the observation light S, however, may account for a majority of lights having wavelengths other than the predetermined wavelength, it passes through the first mirror 25 and leads to the second mirror 26.

The second mirror 26 is a mirror that is arranged so as to reflect the observation light S passed through the first mirror 25 and lead the reflected light to the ocular optical system unit 27. The first mirror 25 may consist of a usual mirror or a mirror that can reflect the observation light S and pass the lights having the wavelength of the laser beams L therethrough.

In the event that the mirror is used which can pass the light with the wavelength of the laser beams L therethrough, the laser beams L which were sent from the object optic system unit 23, reflected by the incubator 14 and so on, and again entered into the object optic system unit 23 are not reflected toward the ocular optical system unit 27, thereby preventing adverse influences on the eyes of the observers P, even if the laser beams L would be led to the second mirror 26 without being reflected by the first mirror 25.

The observation light S reflected by the second mirror 26 enters into the ocular optical system unit 27.

The ocular optical system unit 27 is an optic system for enlarging an image formed by the observation light S. The observation light L incoming into the pupil of the eye of the observer P through an ocular lens 31 equipped inside may be recognized visually.

The cell detachment device A according to the working embodiment of the present invention having the arrangement as described above enables the observer P to observe a state of the cells 16 within the incubator 14 and the cells 16 to be detached from the scaffold 15 by irradiating the cell-adhering scaffold 15 with the laser beams L.

4. Preparatory Experiment Before Cell Culture:

The following is a description regarding an observation about a variation of the scaffold formed in the incubator by the irradiation of the scaffold with the laser beams using the cell detachment device A having the structure as described above.

This experiment was carried out as a preparatory experiment for a cell detachment experiment that follows. In this experiment, an incubator was used which has not been used for cell culture.

As the incubator, there was used herein a dish that was used above for treatment in 10 cycles as described under the title "2. Preparation of the incubator" above. In this experiment, the laser beams were irradiated in such a manner that a laser light of near infrared light of approximately 4 ns exited in a pulse shape at even intervals of 20 times per second from a device (PolarisIII; New Wave Research; Nd: YV04, wavelength, 1064 nm). In the main experiment, however, the laser beams were irradiated in a cross form to the scaffold in order to facilitate a ready confirmation of the result of the experiment. The confirmation was made by observing the result visually through an optical-fluorescent microscope (ECLIPSE, TE2000-U; NIKON®). The result is shown in FIG. 5.

Figure 5:
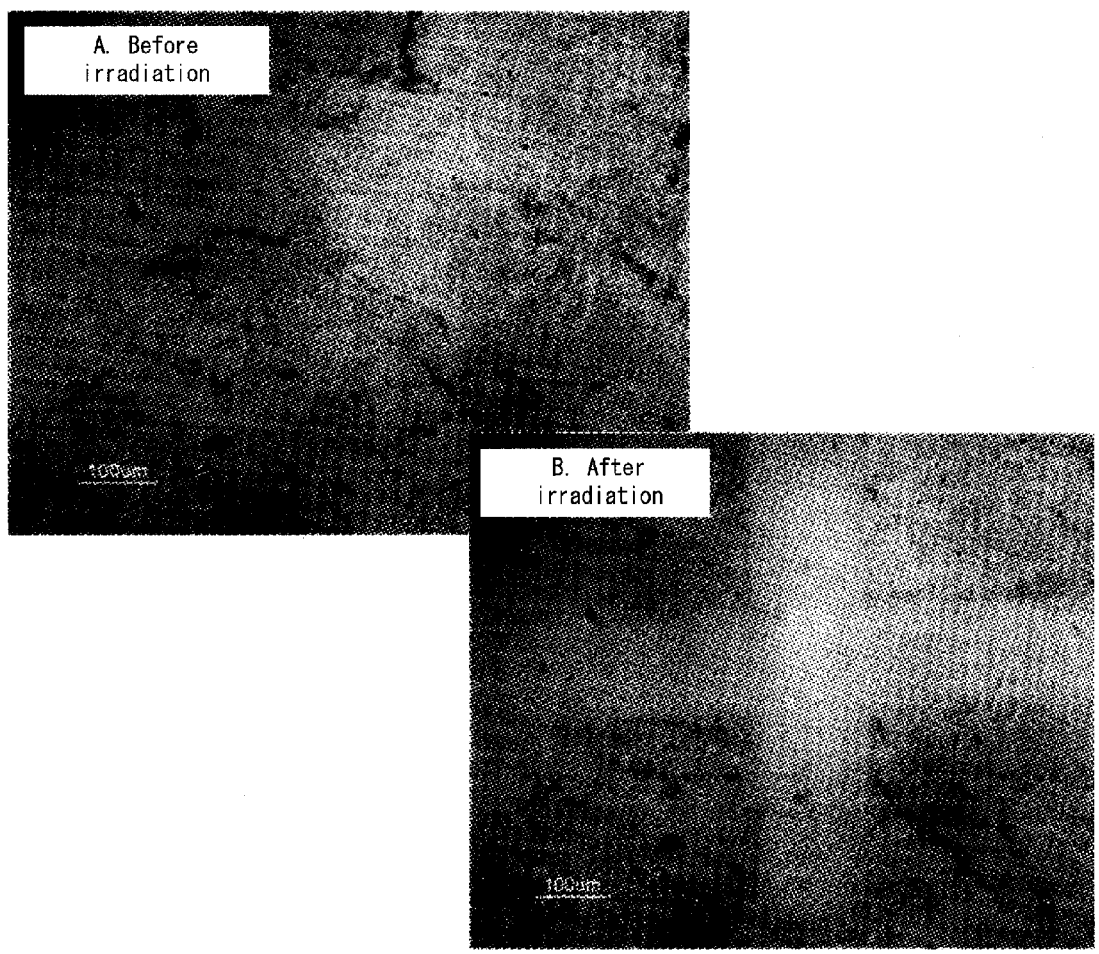
FIG. 5 is an explanatory drawing showing a manner of the destruction of the cell adhesion factor before and after irradiation with laser beams.

FIG. 5A shows a state of the scaffold before irradiation with the laser beams, and FIG. 5B shows a state of the scaffold after irradiation therewith. As is found in FIG. 5, it was visually confirmed that the scaffold was caused to disappear along a locus of irradiation with the laser beams. At the same time, a thermography was used together for a measurement for the temperature of the scaffold during irradiation with the laser beams. As a result of the measurement for the temperature thereof, no changes of the temperature were detected. This implies that the SWNT used as a thermal source caused an ablation and protected the cells from damages to be otherwise caused by the heat.

5. Detachment Experiment by Cell Culture:

Thereafter, an experiment was carried out in order to observe whether the cell was detached or not by incubating cells in the incubator and irradiating the scaffold with laser beams.

The incubator and laser beams used were as described above. The laser beams were irradiated in a spot-like shape to a region of the scaffold to which plural cells (approximately 10 to 20 cells) adhered. As cells to be cultured, HeLa cells were used, and they were incubated in a conventional way. A state of adhesion of the cultured cells to the scaffold was observed. The result is shown in FIG. 6.

FIG. 6A shows a state of the cultured cells before irradiation with the laser beams, and FIG. 6B shows a state of the cultured cells after irradiation therewith. As will be found from a comparison between the results as shown in FIGS. 6A and 6B, it was observed that the cell was detached from the site of the scaffold which was irradiated with the laser beams, where a white arrow symbol is indicated in FIG. 6B. This is considered that the cell was brought into a detached state from the scaffold due to the shock waves caused to be generated by the photothermal conversion of the SWNT and then detached from the scaffold. It is also considered that the SWNT was decomposed by its violent thermal vibration and converted into amorphous carbon and $CO_2$, causing to occur a phenomenon of bringing the cell into a detached state and being detached from the scaffold. In this experiment, the cell detached was stayed in a state floating in the liquid culture medium and then collected readily from the liquid culture medium.

6. Experiment for Confirming the Life or Death of the Detached Cell:

The HeLa cell collected after having been detached in the above experiment was then inoculated on a 96-well microplate and continued to incubate in order to confirm the life or death of the cell detached.

More specifically, the confirmation of the life or death of the detached cell was performed by visually confirming the adhesion and multiplication of the detached cell by a microscope and measuring its cell activity by MTT assay.

FIG. 7 shows a result of the visual confirmation by the microscope. FIG. 7(a) indicates a microscopic image (control) of the cells that were incubated by collecting the liquid culture medium from the incubator from which no cultured cells were detached. FIG. 7(b) indicates a microscopic image of the cells that were incubated by collecting the liquid culture medium from the incubator from which the cultured cell was detached. As will be found by a comparison between the results as shown in FIGS. 7(a) and 7(b), the microscopic image shown in FIG. 7(a) where no cultured cell was detached indicates neither multiplication nor presence of any cell. On the other hand, the microscopic image shown in FIG. 7(b) where the cultured cell was detached indicates the presence of the cells. In other words, the adhesion of the cells to the scaffold and the multiplication thereof were confirmed.

Figure 8:
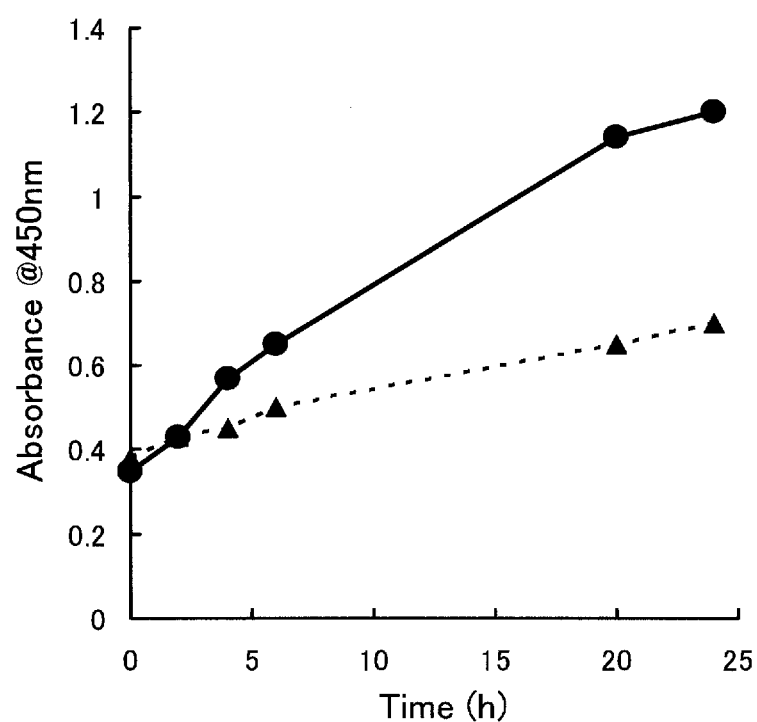
FIG. 8 is a line graph showing the result of a measurement for a cell activity of the detached cell.

The result of the MTT assay is shown in FIG. 8. The MTT used herein is a kind of tetrazolium salts, i.e., 3-(4,5-dimethylthiazol-2-yl)-2,5-diphenyltetrazolium bromide, which is solubilized in water turning yellow and converted into formazan by the action of a dehydrogenase present in the mitochondria of a cell upon uptake into a living cell. The resulting formazan has an absorption wavelength at 450 nm so that the measurement for its absorbance enables a determination of the life or death of the cell. As shown in FIG. 8, the solid line indicates a periodical variation in the absorbance of the liquid culture medium which were collected from the incubator, where the cell was detached, and then incubated. On the other hand, a broken line indicates a periodical variation of the liquid culture medium in the absorbance when the liquid culture medium where no cell was detached was collected and then incubated.

As shown in FIG. 8, the system of the cell detachment as indicated by the solid line shows an increase of the absorbance at 450 nm as time elapses, compared to the control as indicated by the broken line.

As described above, the results of the visual observation by the microscope and the MTT assay reveal that the cell detached into the liquid culture medium by the detachment method of the cultured cells according to Example 1 sustained its vital activity.

Example 2

This example is to explain an example where the cell adhesion factor forming the scaffold is structured with a mixture of the SWNT with a collagen.
1. Hydrophilization Treatment of SWNT:

The SWNT structuring a part of the cell adhesion factor was hydrophilized with ozone. The SWNT (HIPCO®, CNI) was spread uniformly over on the inner bottom of a dish (TRADE FLAT MARK). The dish was then placed in a UV ozone cleaner and irradiated with ultraviolet light for 10 minutes in the presence of oxygen, followed by stirring with a spatula and repeating this operations six times to perform the hydrophilization of the SWNT.
2. Preparation of Cell Adhesion Factor:

In this example, a mixture of collagen with SWNT was used as the cell adhesion factor.

The mixture was prepared by adding 2.2 mg of SWNT hydrophilized as above with 3 mg of collagen (Nitta Gelatin K.K.; pH 3, 0.3% Cellmatrix Type I-A) to 10 ml of water, and the resulting mixture was subjected to ultrasonic treatment for 2 minutes with a probe-type sonicater (TOMY, UD-200), thereby dispersing and dissolving the mixture. The resulting uniform mixture was then centrifuged at 1,000×g for 60 minutes with a table top-type high-speed refrigerated centrifuge (Model: 3K30C; Kubota Shoji K.K.), followed by collecting the supernatant as a collagen/SWNT solution.
3. Preparation of Incubator:

The collagen/SWNT solution prepared above was then dropwise added to a dish (TRADE FLAT MARK) forming the scaffold on an inner bottom of the dish, followed by drying the scaffold.

A culture medium (Minimum Essential Medium (MEM: Nitta Gelatin K.K.; 10-fold concentrated medium)(0.1 ml) was added to 0.8 ml of the cooled collagen/SWNT solution in a clean bench, and the mixture was then stirred with a pipetting in such a manner that no bubbles occur, followed by adding 0.1 ml of a reconstructing buffer and then re-stirring the resulting mixture with the pipetting. This stirring work was carried out quickly without causing the temperature of the cooled collagen/SWNT solution to rise.

Thereafter, 0.05 ml of the resulting mixture was dropwise added to the inner bottom of a dish, and the excessive amount of the mixture was suctioned. The dish was then placed in an incubator warmed at 37° C. for 10 minutes to dryness, and the dish was used for further experiments as an incubator having a scaffold.
4. Experiment for Detaching the Cultured Cell:

The cells were then incubated in the incubator prepared above, and whether the cultured cells were detached or not was observed by irradiating the scaffold using the cell detachment device A prepared above.

The laser beams were irradiated from a laser beam emitter (BL-106C; manufacturer: Spectra; ND: YV04; wavelength 1,064 nm; output, 200 mW). The cells used herein were HeLa cells, and they were incubated in a conventional way after previously confirming the adhesion of the cells to the scaffold. The confirmation was carried out by visually observing the cells with an optical-fluorescent microscope (ECLIPSE, TE2000-U; NIKON® K.K.). The result is shown in FIG. 9.

FIG. 9(A) shows a state of the cultured cells before irradiation with the laser beams, and FIG. 9(B) shows a state of the cultured cells after irradiation therewith. As will be found from a comparison between the results as shown in FIGS. 9(A) and 9(B), the detachment of the cultured cell was observed at a portion at which the laser beams had been irradiated (the portion indicated by a white arrow symbol in FIG. 9). This is considered that the cultured cell was brought into a detached state and detached by the shock waves generated by the photothermal conversion of the SWNT upon the irradiation with the laser beams. At the same time, it is also considered that the SWNT was decomposed by its violent thermal vibration and converted into amorphous carbon and $CO_2$, causing to occur a phenomenon of bringing the cell into a detached state and consequently being detached from the scaffold. The cell detached in this experiment was stayed in a state floating in the liquid culture medium and then collected readily from the liquid culture medium.
5. Experiment for Confirming the Life or Death of the Detached Cell:

The HeLa cell collected after having been detached in the above experiment was then inoculated on a 96-well microplate and continued to incubate in order to confirm whether the collected cell was alive or dead. In substantially the same manner as in Example 1, the life or death of the detached cell was performed by the visual confirmation of the adhesion and multiplication of the collected cultured cell with a microscope and the measurement for its cell activity by the MTT assay.

The visual confirmation reveals that a microscopic image of a system where no cell was detached demonstrates neither a presence nor multiplication of any cell. On the other hand, a microscopic image of a system where the cultured cell was detached demonstrates the presence of the cultured cell. In other words, there were confirmed the adhesion of the cultured cell to the scaffold and the multiplication thereof as well.

Figures 10, 11:
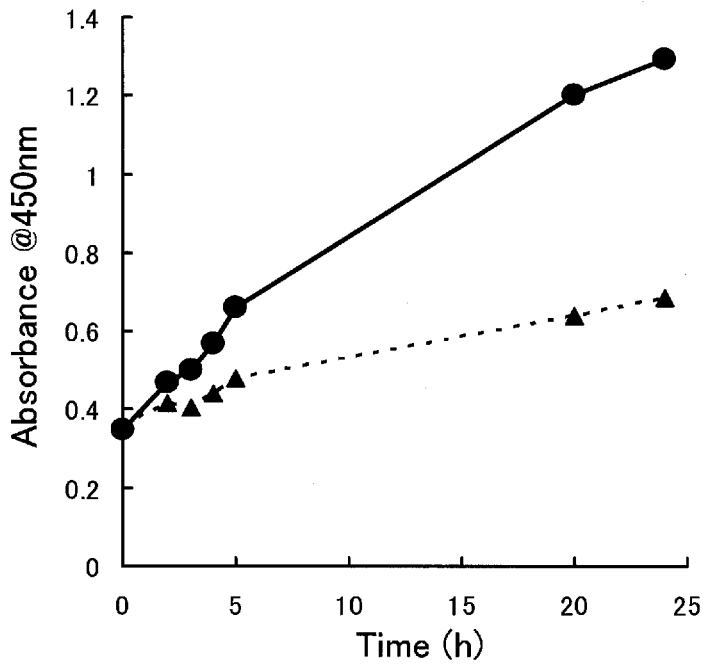
FIG. 10 is an explanatory drawing showing the result of an assay for cell activity of the detached cell.
FIG. 11 is a table showing a connection between an output of laser beams and a state of a cell.

FIG. 10 shows the results of the MTT assay. As shown in FIG. 10, it was found from a comparison of the result indicated as a control by the broken line with the result indicated by the solid line that the system detaching the cell increases the absorbance at 450 nm as time elapsed.

From the results of the visual observation with the microscope and the MTT assay, the cell detached into the liquid culture medium by the cell detachment method according to Example 2 was found to sustain its vital activity.

Example 3

This example indicates an example in which a single cell was irradiated with the laser beams and caused to adhere to a rear surface of a dish lid, followed by a selective collection of the adhered single cell. In this example, the cell adhesion factor and the incubator were prepared in substantially the same manner as done in Example 1. A description of them is omitted herefrom accordingly.

Example of collection of cell upon irradiation with laser beams having different wavelengths:

HeLa cells were incubated in a dish, and the laser beams having different wavelengths were sent from the cell detachment device A upon a site of the scaffold of the dish, in which the number of the cell adhered thereto was set to only one cell, thereby detaching the single cell adhered to the scaffold.

As the wavelengths of the laser beams, there were used herein three different laser beams having a wavelength of 254 nm (an ultraviolet laser beam), 785 nm (a visual laser beam), and 1,064 nm (a near infrared laser beam). The output of each laser beam was 50 mw. The adhesion of a single cell to the rear surface of the dish was recognized in each case by the irradiation with each of the three different laser beams. In other words, it was found that the single cell could be detached from plural cells and caused to adhere to the rear surface of the dish. The cell collected in this example from the rear surface of the dish, however, was considered dead because it did not multiply by re-incubation.

From the above results, it was also found that the wavelength of the laser beam is not limited to a particular one as long as it has a predetermined energy. It is found advisable, however, that the wavelength of the laser beam to be irradiated is in the range of near infrared that little affects or does not much affect cells adversely from a viewpoint of handling living cells.

Example of collection of cells upon irradiation with laser beams having different intensities:

HeLa cells were incubated in a dish, and the adhered cells were detached by irradiation with near infrared laser beams outgoing with different outputs.

The outputs of the laser beams irradiated were six different outputs: 30 mw, 35 mw, 39 mw, 40 mw, 500 mw and 510 mw. The wavelength of each of the laser beams was in a near infrared range of 1,064 nm. The results are shown in FIG. 11.

As shown in FIG. 11, it was observed that no cell was detached in the event where the output of the laser beams was 30 mw, while the cell was detached when the laser beams was irradiated with the output of 35 mw. It is thus found that the output of the laser beams is required to be generally 35 mw or higher for detaching the cells using the near infrared laser beams, although it may depend upon the kind of the cells, the cell adhesion factor forming the scaffold, a viscosity of the liquid culture medium, and the like.

On the other hand, in the event where the laser beams were irradiated with the output of 39 mw, no adhesion of the cultured cell to the rear surface of the dish lid was recognized, while the adhesion of the cultured cell to the rear surface thereof when the laser beams were irradiated at the output of 40 mw (see FIG. 12). This indicates that the single cell was isolated from the plural cultured cells. It is further found that the output of the laser beams above approximately 40 mw was required to let the single cell catapult off from the liquid surface of the liquid culture medium and detach it from the other cells, although it may depend to some extent upon the kind of the cells to be incubated, the cell adhesion factor forming the scaffold, a viscosity of the liquid culture medium, and so on. It was further found that the cultured cell could be collected at the outputs of 500 mw and 510 mw, respectively, in substantially the same manner as done at the output of 40 mw.

As a result of re-incubation of each of the cells collected, it was confirmed that the cells collected from the liquid culture medium after detachment by irradiation with the laser beams having the output of 35 mw and 39 mw, respectively, were alive because they were found to multiply. On the other hand, the cells detached by the output of 40 mw and collected from the rear surface of the dish lid were considered dead because they did not multiply. The cells collected by the output of 500 mw and 510 mw were considered dead because each of them did not multiply.

Verification was performed by PCR by amplifying the gene of the cell acquired by irradiation with the laser beams at the output of 500 nm. One of housekeeping genes, i.e., human GAPDH gene present always in the HeLa cells, was subjected to amplification by RT-PCR.

Among the plural cells incubated in the manner described above, a predetermined cell was treated so as to catapult off from the liquid culture medium by the method described above and caused to adhere to an inner wall surface of a lid (an inner diameter of approximately 1 cm) of a 1.5-ml plastic tube disposed as a cell collection substrate.

A 20-30 µl aliquot of a cell lysis buffer (APPLIED BIOSYSTEMS®) was dispensed and injected into the 1.5-ml plastic tube, and the cells attached to the lid was added to the buffer and dissolved therein, followed by centrifugation, refrigeration and re-fusion.

Thereafter, cDNA was prepared by carrying out reverse transcription PCT with CELLS-TO-CDNA™II Kit (APPLIED BIOSYSTEMS®) using mRNA eluted into the buffer as a template.

The real time PCR was then performed using the resulting cDNA as a template, human GAPDH primer as a primer, and SYBR® Green I as a fluorescent pigment for detecting DNA. The result is shown in FIG. 13.

Figure 13:
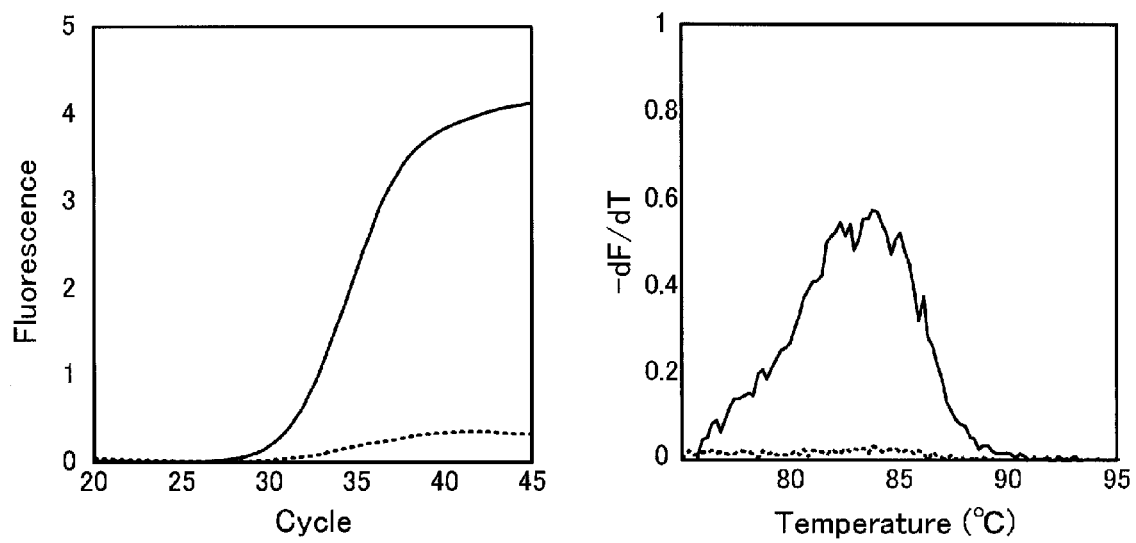
FIG. 13 is graphs showing the results of a RT-PCR using the cell recovered.

As shown in FIG. 13, the left-hand table indicates an amplification curve of PCR products, and the right-hand curve is a fusion curve of the human GAPDH. In FIG. 13, the sample is indicated by the solid line, and a control is indicated by a broken line.

As shown in FIG. 13, it was found that the amplification of the predetermined gene (for example, human GAPDH gene) could be made using the cells obtained by the output of 500 mw.

A similar experiment was carried out using the cells acquired by the output of 40 mw and 510 mw, respectively. As a result, it was found that the cells acquired by the output of 40 mw were amplified in substantially the same manner as the cells collected by the output of 500 mw, while the cells acquired by the output of 510 mw could not be amplified in the manner similar thereto.

As described above, the cell detachment method for the detachment of the cultured cells according to the present invention enables the selective detachment of the cells adhered to a scaffold formed with a cell adhesion factor containing at least a nanocarbon by irradiating a range of the scaffold to which a predetermined cell or cells adheres or adhere with laser beams in a spot shape, thereby bringing the cell or cells into an adhesion-free state by shock waves generated by the heat produced by the photothermal conversion of the nanocarbon by the irradiation with the laser beams and allowing the cell or cells to be selectively detached.

In summary, each of the working embodiments described above is solely illustrative of the present invention, and the present invention is interpreted as being not limited to the above working embodiments. Therefore, as a matter of course, any other modifications of each of the above working embodiments including any changes of designs and so on are encompassed within the scope of the present invention as long as they do not depart from the technical concept of the present invention.

In the above working embodiments of the present invention, the HeLa cells were taken as an example of the cultured cells. It is to be understood without doubt that any other adherent cells are applicable.

In the above working embodiments of the present invention, the single-walled carbon nanotube was taken as an example of the nanocarbon to be used for the cell adhesion factor of the scaffold, however, the cell adhesion factor is not limited thereto. Any substance having a structure with a number of five-membered, six-membered (heterocyclic) or seven-membered cyclic carbons connected to each other and capable of efficiently inducing the photothermal conversion can also be used appropriately.

The invention claimed is:

1. A method for the detachment of a cultured cell for selectively detaching an adherent cell cultured in a liquid culture medium in an incubator, comprising:
   forming a scaffold for attaching the adherent cell with a cell adhesion factor containing at least a nanocarbon; and
   irradiating a site of the scaffold to which the adherent cell adheres with a laser beam in a spot shape, thereby causing the site of the scaffold to disappear by heat produced by a photothermal conversion of the nanocarbon caused to occur by irradiation with the laser beam and causing the site of the scaffold irradiated with the laser beam to work as an ablator to bring the adherent cell located in the site of the scaffold into a detached state while protecting the cell from the heat;
   wherein the laser beam is irradiated at an intensity that allows the detached cell to catapult through the liquid surface of the liquid culture medium into air by an action of the shock waves.

2. The method for the detachment of the cultured cell as claimed in claim 1, wherein:
   plural cells adhere to the scaffold; and
   a region of the scaffold to which a single cell adheres is irradiated with the laser beam, isolating the single cell from the other plural cells.

3. The method for the detachment of the cultured cell as claimed in claim 1, wherein:
   the incubator is provided with an opposite surface facing and opposite to the liquid surface of the liquid culture medium; and
   the cell catapulted off from the liquid surface of the liquid culture medium by means of the shock waves generated by irradiation with the laser beam is caused to adhere to the opposite surface.

4. The method for the detachment of the cultured cell as claimed in claim 1, wherein said laser beam has a wavelength in a near infrared region.

5. The method for the detachment of the cultured cell as claimed in claim 1, wherein said nanocarbon is a single-walled carbon nanotube (SWNT).

6. A method for the detachment of a cultured cell for selectively detaching an adherent cell cultured in a liquid culture medium in an incubator, comprising: forming a scaffold a scaffold for attaching the adherent cell with a cell adhesion factor containing at least a nanocarbon; and
   irradiating a site of the scaffold to which the adherent cell adheres with a laser beam in a spot shape, thereby causing the site of the scaffold to disappear by heat produced by a photothermal conversion of the nanocarbon caused to occur by irradiation with the laser beam and causing the site of the scaffold irradiated with the laser beam to work as an ablator to bring the adherent cell located in the site of the scaffold into a detached state while protecting the cell from the heat;
   wherein an amount of said liquid culture medium is adjusted to a depth that allows the adherent cell attached to the site of the scaffold to catapult a through the liquid surface of the liquid culture medium into air by means of shock waves delivered by irradiation with the laser beam.

7. The method for the detachment of the cultured cell as claimed in claim 6, wherein:
   plural cells adhere to the scaffold; and
   an region of the scaffold to which a single cell adheres is irradiated with the laser beam, isolating the single cell from the other plural cells.

8. The method for the detachment of the cultured cell as claimed in claim 6, wherein:
   the incubator is provided with an opposite surface facing and opposite to the liquid surface of the liquid culture medium; and
   the cell catapulted off from the liquid surface of the liquid culture medium by means of the shock waves generated by irradiation with the laser beam is caused to adhere to the opposite surface.

9. The method for the detachment of the cultured cell as claimed in claim 6, wherein said laser beam has a wavelength in a near infrared region.

10. The method for the detachment of the cultured cell as claimed in claim 6, wherein said nanocarbon is a single-walled carbon nanotube (SWNT).

* * * * *